United States Patent [19]

Stone et al.

[11] 4,294,968

[45] Oct. 13, 1981

[54] METHOD FOR PREPARING α-PICOLINE FROM 5-OXOHEXANENITRILE

[75] Inventors: Frederick C. Stone; Gary G. Schupska, both of Midland, Mich.

[73] Assignee: The Dow Chemical Company, Midland, Mich.

[21] Appl. No.: 166,512

[22] Filed: Jul. 7, 1980

Related U.S. Application Data

[63] Continuation of Ser. No. 53,635, Jun. 29, 1979, abandoned.

[51] Int. Cl.$^3$ .................. C07D 213/08; C07D 213/09
[52] U.S. Cl. .................................... 546/251; 546/348; 546/349

[58] Field of Search ....................... 546/349, 348, 251

[56] References Cited

U.S. PATENT DOCUMENTS 3,007,931 11/1961 Simpson et al. .................... 546/347

FOREIGN PATENT DOCUMENTS 1304155 1/1973 United Kingdom ............... 546/349

Primary Examiner—Alan L. Rotman
Attorney, Agent, or Firm—Charles J. Enright

[57] ABSTRACT

The catalytic method of preparing α-picoline from 5-oxohexanenitrile is improved by using as the catalyst carbon-supported palladium.

4 Claims, No Drawings

METHOD FOR PREPARING α-PICOLINE FROM 5-OXOHEXANENITRILE

CROSS-REFERENCE TO RELATED APPLICATION

This is a continuation of application Ser. No. 53,635, filed June 29, 1979, now abandoned.

BACKGROUND OF THE INVENTION

1. Field of the Invention

This invention relates to the manufacture of α-picoline from 5-oxohexanenitrile (OHN).

2. Description of the Prior Art

British Pat. No. 1,304,155 teaches the preparation of α-picoline by contacting OHN with an alumina-supported palladium catalyst. The conversion of OHN is good but the selectivity to α-picoline is less than desirable.

Simpson et al., U.S. Pat. No. 3,007,931, teach the preparation of unsaturated, heterocyclic nitrogen bases of the pyridine and quinoline series. These compounds are prepared by contacting various nitriles with any one of a number of different dehydrogenation catalysts. The catalysts are transition metals or metal oxides of Group IV-A, V-A, VI-A and VIII of the Periodic Table and are typically supported on chips of clay plate. The preparation of α-picoline from OHN is not specifically taught.

SUMMARY OF THE INVENTION

According to this invention, the method of preparing α-picoline comprising contacting under dehydrogenation conditions OHN with a dehydrogenation catalyst is improved by the using as the catalyst carbon-supported palladium. This method is highly selective for α-picoline without sacrifice of OHN conversion (as compared to methods employing alumina-supported palladium).

DETAILED DESCRIPTION OF THE INVENTION

The method of this invention is graphically depicted as follows:

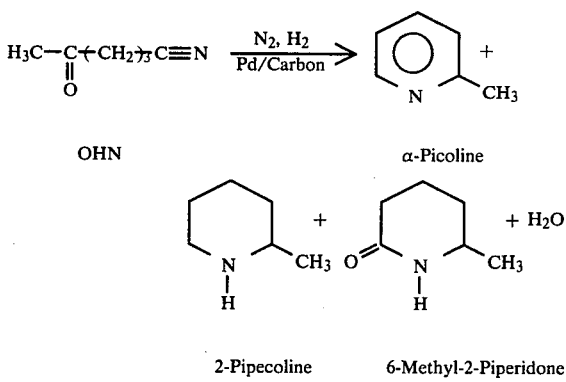

Typically, the reaction is conducted in the gas phase over a catalyst bed with the OHN diluted with hydrogen and nitrogen. A fixed-bed reactor is usually employed and the reaction is usually conducted at elevated temperature and pressure. The reaction temperature and pressure are each independently variable and can be adjusted to convenience. However, preferred rates of reaction are typically obtained with a minimum temperature of about 200° C. and preferably of about 230° C. A maximum temperature is typically about 330° C. and preferably about 290° C. The pressures employed can also vary widely but are typically between about 0 and 20 psig. Autogenous pressure is preferred.

The reactants of this method are well-known. OHN is readily prepared from acetone and acrylonitrile (U.S. Pat. No. 3,816,503). Hydrogen is normally admixed with vaporized OHN prior to their contact with the catalyst. Nitrogen is an optional, inert (nonreactive) component of the reaction mixture and is used generally to regulate the hydrogen partial pressure. This partial pressure has some influence on OHN conversion and α-picoline selectivity; generally the higher the partial pressure, the higher the OHN conversion and the higher the α-picoline selectivity. However, at some point, the OHN conversion and α-picoline selectivity diverge and determination of this point for any given set of reaction conditions is well within the skill of the ordinary artisan. When used, the nitrogen, like the hydrogen, is generally admixed with the vaporized OHN prior to their contact with the catalyst.

The catalyst here used is palladium supported on carbon, normally in granular form. There are many commercial sources of palladium on carbon catalysts, such as Englehard, and most such commercial catalysts can be here used. Alternatively, the catalysts can be prepared by simply adding a soluble palladium salt to carbon in an aqueous medium, agitating and then recovering the palladium-coated carbon. Virtually any form of carbon can be used but charcoal and graphite are the preferred forms. Likewise, the surface area of the carbon can vary considerably; carbon having a surface area of at least about 50 $m^2/g$ is preferred. These catalysts can be used repeatedly to effect high conversion of OHN with good selectivity to α-picoline. Repeated usage does tend to reduce catalytic activity but this can be offset by adjusting the reaction temperature and/or hydrogen partial pressure slightly upward. The catalysts are regenerated by contacting with air at elevated temperatures, e.g., 270° C.

The principal method product, like the principal method reactant, is also well-known in the art. α-Picoline is a valuable intermediate in many pharmaceuticals, insecticides and plant nutriments. The method of this invention effects the production of α-picoline with greater selectivity without sacrifice of OHN conversion. This is accomplished principally by reducing the production of the unwanted by-products 2-pipecoline and 6-methyl-2-piperidone. The prior art methods for preparing α-picoline with palladium on alumina produce significant amounts of these by-products, but particularly the piperidone.

The method of this invention can be conducted on both a batch or continuous operation. A continuous method is typically more convenient and economically attractive than a batch method and thus a continuous method is preferred over a batch method.

The following examples are illustrative embodiments of this invention. Unless indicated otherwise, all parts and percentages are by weight.

SPECIFIC EMBODIMENT

Example and Control: Procedure

A series of reactions was conducted in a laboratory-scale fixed-bed reactor containing a catalyst bed of supported palladium. The reactor was preheated to a designated temperature with a nitrogen purge and then vaporized OHN, hydrogen and nitrogen, all premixed, were introduced and passed through the reactor. The exit gas from the reactor was analyzed by gas chromatography. The specific conditions for each case are reported in the table.

TABLE

|  | Example | Control |
|---|---|---|
| Catalyst[1] | 1% Pd/Carbon | 0.3% Pd/Al$_2$O$_3$ |
| OHN Space Velocity |  |  |
| (g/cc-Cat-hr) | 0.10 | 0.07 |
| (g/g-Pd-hr) | 20.2 | 23.3 |
| Temp (°C.) | 240 | 240 |
| Pres (psig) | 4.7 | 4.7 |
| H$_2$:OHN (moles) | 1.6 | 1.6 |
| N$_2$:OHN (moles) | 4.7 | 4.6 |
| Total Operation (hours) | 20 | 19 |
| Product Mix (wt. %, H$_2$ and N$_2$ free basis) |  |  |
| α-Picoline | 30.5 | 19.4 |
| 2-Pipecoline | 2.1 | 0.7 |
| 6-Methyl-2-piperidone | 0.9 | 11.1 |
| OHN | 57.7 | 58.1 |
| H$_2$O | 6.3 | 3.9 |
| Unknowns | 2.5 | 6.8 |
| % Conv. of OHN[2] | 42.3 | 41.9 |
| % Sel. to α-Pic[3] | 86.0 | 55.3 |
| % Sel. to 2-Pip[4] | 5.6 | 1.9 |
| % Sel. to 6-MP[5] | 2.2 | 27.0 |

[1] 1% Pd/Carbon: 4–8 mesh by Englehard
0.3% Pd/Al$_2$O$_3$: ⅛" α-alumina pellets by Harshaw
[2] % Conversion of 5-oxohexanenitrile
[3] % Selectivity to α-picoline
[4] % Selectivity to 2-pipecoline
[5] % Selectivity to 6-methyl-2-piperidone
% Selectivity to all components calculated as moles of component divided by moles of OHN converted and the resulting quotient multiplied by 100.

Although the palladium loading of the Example (1 percent) was different from the palladium loading of the Control (0.3 percent), the results of each are directly comparable because the OHN space velocity of each was adjusted accordingly. As is reported in the Table, the g/cc-Cat-hr and g/g-Pd-hr for both the Example and Control were essentially the same meaning that essentially the same number of OHN and H$_2$ molecules contacted the palladium in the Example as in the Control.

The data in the above Table demonstrate the improved selectivity to α-picoline obtained by using palladium on carbon as the catalyst. Of the converted OHN, 86.0 percent was α-picoline as compared to only 55.3 percent from the palladium on alumina catalyst. This improved selectivity was achieved without any sacrifice of OHN conversion. The improved selectivity was a result of producing significantly lower amounts of 6-methyl-2-piperidone.

Although the instant invention has been described in considerable detail by the above example and control, this detail is for the purpose of illustration only and is not to be construed as a limitation upon the scope of this invention as defined by the appended claims.

What is claimed is:

1. In a method of preparing α-picoline comprising contacting under dehydrogenation conditions 5-oxohexanenitrile with a palladium dehydrogenation catalyst, the improvement wherein the catalyst is palladium on a carbon support.

2. The method of claim 1 wherein the carbon support has a surface area of at least about 50 m$^2$/g.

3. The method of claim 2 wherein the carbon support is in a granular form.

4. The method of claim 3 wherein the carbon support is charcoal.

* * * * *